United States Patent
Ham et al.

(10) Patent No.: US 7,830,511 B2
(45) Date of Patent: Nov. 9, 2010

(54) APPARATUS AND METHOD FOR MEASURING POLARIZATION DIRECTION OF POLARIZING PLATE

(75) Inventors: Yong Sung Ham, Anyang-si (KR); Jong Won Moon, Anyang-si (KR); Jin Kwan Jeong, Busan (KR)

(73) Assignee: LG Display Co., Ltd., Seoul (KR)

( * ) Notice: Subject to any disclaimer, the term of this patent is extended or adjusted under 35 U.S.C. 154(b) by 671 days.

(21) Appl. No.: 11/819,955

(22) Filed: Jun. 29, 2007

(65) Prior Publication Data

US 2008/0088828 A1   Apr. 17, 2008

(30) Foreign Application Priority Data

Jun. 30, 2006   (KR) ..................... 10-2006-0060963

(51) Int. Cl.
   *G01J 4/00*   (2006.01)
(52) U.S. Cl. ................... 356/364; 356/370; 250/225; 250/341.3
(58) Field of Classification Search ............... 250/225, 250/341.3; 356/364–370
   See application file for complete search history.

(56) References Cited

U.S. PATENT DOCUMENTS 4,699,514 A * 10/1987 Schmidt et al. ............. 356/367
5,627,645 A *  5/1997 Imagawa et al. ............ 356/364

FOREIGN PATENT DOCUMENTS

JP   2005-227019    8/2005
JP   2005-275063   10/2005

* cited by examiner

*Primary Examiner*—Gregory J Toatley, Jr.
*Assistant Examiner*—Iyabo S Alli
(74) *Attorney, Agent, or Firm*—McKenna Long & Aldridge

(57) ABSTRACT

A polarization direction measuring apparatus includes: a first polarizing plate having an unknown polarization direction about a reference axis; a sample whose polarization direction is to be measured; a rotatable sample holder on which the sample is mounted in a first direction and a second direction opposite to the first direction, wherein the sample holder rotates the sample along a reference axis in the azimuth direction; a light source that generates light passing though the first polarizing plate and the sample; and a light detector detecting light generated by the light source that passes though the first polarizing plate and the sample.

16 Claims, 9 Drawing Sheets

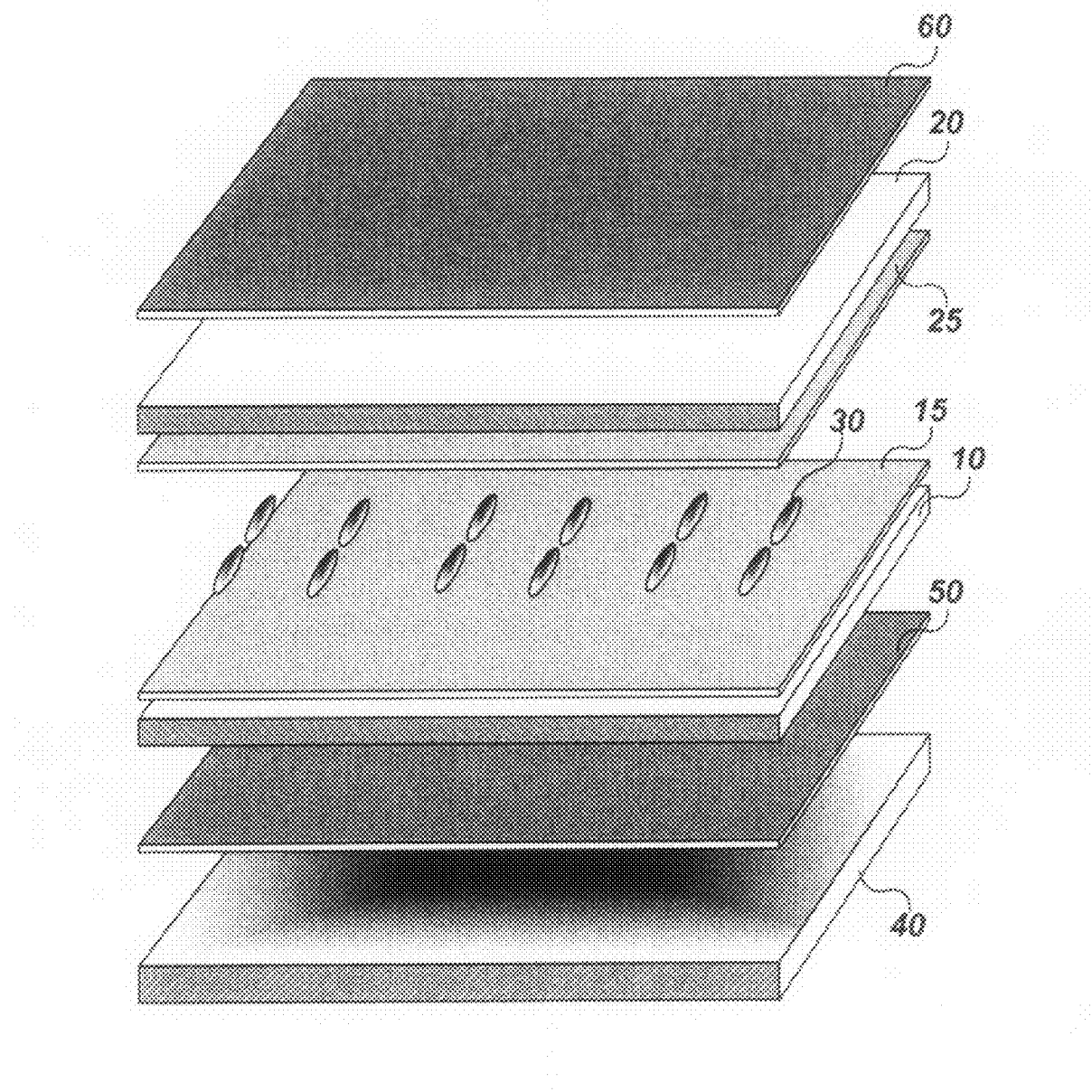

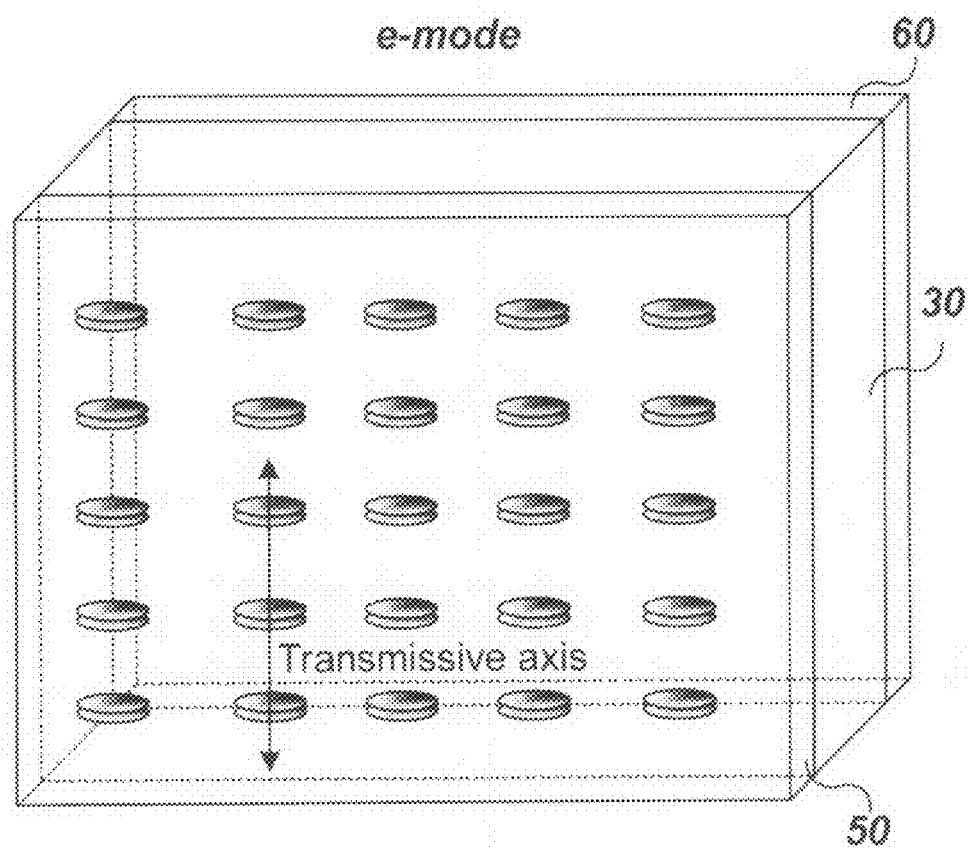

APPARATUS AND METHOD FOR MEASURING POLARIZATION DIRECTION OF POLARIZING PLATE

This application claims the benefit of Korean Patent Application No. 10-2006-0060963 filed on Jun. 30, 2006, which is hereby incorporated by reference for all purposes as if fully set forth herein.

BACKGROUND OF THE INVENTION

1. Field of the Invention

This document relates to a display apparatus, and more particularly, to an apparatus and a method for measuring a polarization direction of a polarizing plate for a liquid crystal display.

2. Discussion of the Related Art

Liquid crystal displays are generally devices displaying an image using optical anisotropy and birefringence properties of liquid crystal molecules.

In a liquid crystal display, two substrates each having electrodes for generating electric field face each other so that the surfaces of the two substrates on which the electrodes are formed are opposite to each other, and a liquid crystal material is injected between the two substrates.

Arrangement of the liquid crystal molecules is changed by an electric field obtained by applying a voltage to the electrodes, and thus the liquid crystal display displays an image by controlling the quantity of light transmitted through the substrates.

A thin film transistor-liquid crystal display (TFT-LCD) using thin film transistors (TFT) as switching devices has been generally used.

In the TFT-LCD, white light generated in a backlight unit passes through liquid crystal pixels such that transmittance of the white light is controlled. Then, a color image is displayed using additive color mixtures of light transmitted through red (R), green (G) and blue (B) color filter layers positioned on the liquid crystal pixels.

A display level of the TFT-LCD is determined by controlling the quantity of transmitted or reflected light depending on the intensity of electric field in each pixel.

Because characteristics of the liquid crystal display depend on the polarization state of a first polarizing plate and a second polarizing plate set in a cross-Nicol configuration, optimum designs of the first polarizing plate and the second polarizing plate are necessary and the polarization directions of the first and second polarizing plates have to be accurately known.

However, when the polarization directions of the first polarizing plate and the second polarizing plate are not accurately controlled, the amount of light passing through a liquid crystal layer of the liquid crystal display is not accurately controlled. This leads to a reduced image quality of the liquid crystal display.

FIG. 1 illustrates a configuration of an apparatus for measuring a polarization direction of a polarizing plate of a related art liquid crystal display.

Referring to FIG. 1, the related art polarization direction measuring apparatus includes a light source 71, a first polarizing plate 72, a sample holder 73, a sample 74, and a light detector 75. Light is generated by the light source 71, and the light detector 75 detects the quantity of light passing through the first polarizing plate 72 and the sample 74.

Referring to FIG. 1, the related art polarization direction measuring apparatus includes the first polarizing plate 72, of which a polarization direction is accurately known, and the sample holder 73 capable of accurately positioning a sample 74 along a reference axis thereof.

In other words, the polarization axis of the sample 74 is inclined relative to the polarization axis of the first polarizing plate 72 at a predetermined angle, and the sample 74 is placed along the reference axis of the sample holder 73. Then, while rotating the sample 74 in the azimuth direction, the light detector 75 detects when the minimum quantity of light is detected. Therefore, the angle (i.e., a polarization direction) of the sample 74 inclined relative to the reference axis is obtained.

The related art polarization direction measuring apparatus can accurately measure the polarization direction of the sample 74 when the polarization direction of the first polarizing plate 72 is accurately known.

Further, the reference axis of the sample holder 73 has to be known accurately to mount the sample 74 into the sample holder 73. In other words, the polarization direction of the first polarizing plate 72 and the reference axis of the sample holder 73 have to be known accurately for accurate measurement of the polarization direction of the sample 74. Accordingly, it is difficult to accurately measure the polarization direction of the sample 74.

SUMMARY OF THE INVENTION

Accordingly, the present invention is directed to an apparatus and method for measuring polarization direction of a polarizing plate that substantially obviates one or more of the problems due to limitations and disadvantages of the related art.

An advantage of the present invention is to provide an improved apparatus and method for simply measuring the polarization angle of a polarizing plate.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, as embodied and broadly described, a polarization direction measuring apparatus includes: a first polarizing plate having an unknown polarization direction about a reference axis; a sample whose polarization direction is to be measured; a rotatable sample holder on which the sample is mounted in a first direction and a second direction opposite to the first direction, wherein the sample holder rotates the sample along a reference axis in the azimuth direction; a light source that generates light passing though the first polarizing plate and the sample; and a light detector detecting light generated by the light source that passes though the first polarizing plate and the sample.

In another aspect of the present invention, a method of measuring a polarization direction includes: aligning a light source, a first polarizing plate, and a light detector; inserting a sample into a sample holder in a first direction, wherein a reference axis of the sample holder aligns with the light source and the light detector; rotating the sample holder in an azimuth direction to measure a first angle at which a minimum quantity of light is detected; inserting the sample into the sample holder in a second direction opposite to the first direction; rotating the sample holder in the azimuth direction to measure a second angle at which a minimum quantity of light is detected; and obtaining a value corresponding to one half a difference between the first angle and the second angle to measure a polarization direction of the sample.

It is to be understood that both the foregoing general description and the following detailed description are exemplary and explanatory and are intended to provide further explanation of the invention as claimed.

BRIEF DESCRIPTION OF THE DRAWINGS

The accompany drawings, which are included to provide a further understanding of the invention and are incorporated on and constitute a part of this specification illustrate embodiments of the invention and together with the description serve to explain the principles of the invention. In the drawings:

FIG. 3 schematically illustrates a configuration of a liquid crystal panel;

FIGS. 4A and 4B illustrate polarization modes of a polarizing plate of a liquid crystal display;

DETAILED DESCRIPTION OF PREFERRED EMBODIMENTS

Reference will now be made in detail embodiments of the invention examples of which are illustrated in the accompanying drawings.

Figure 1:
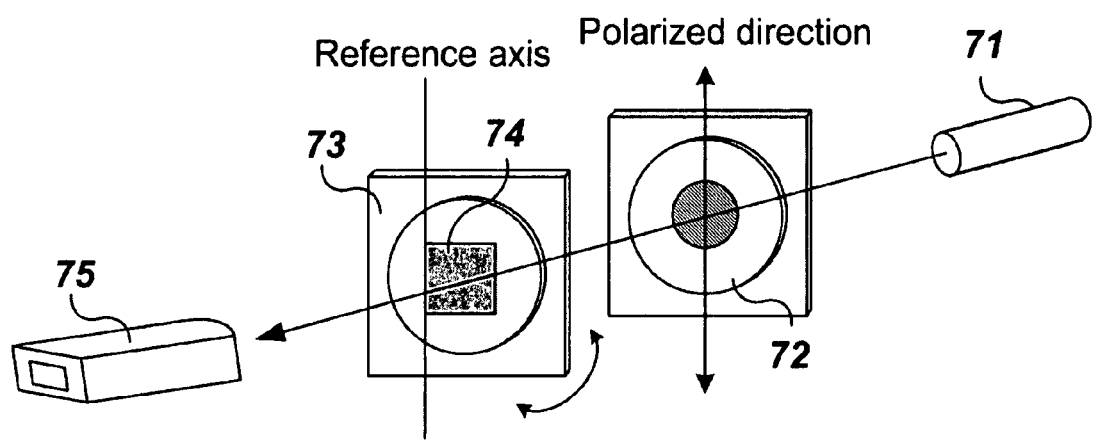
FIG. 1 illustrates a configuration of an apparatus for measuring a polarization direction of a polarizing plate of a related art liquid crystal display.
Figure 2:
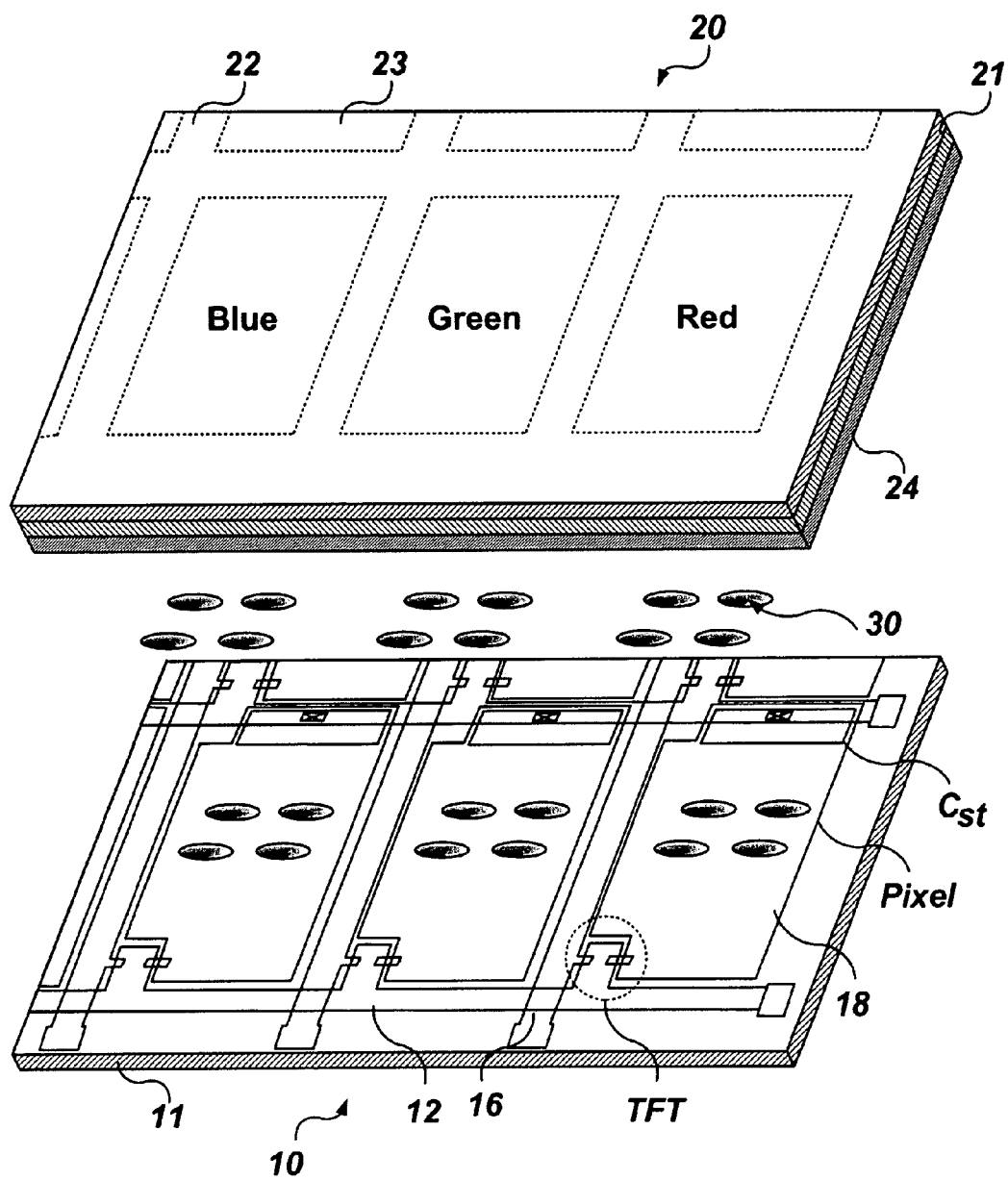
FIG. 2 is a perspective view of a liquid crystal display.

FIG. 2 is a perspective view of a liquid crystal display.

Referring to FIG. 2, a liquid crystal panel positioned inside the liquid crystal display includes a first substrate 10 and a second substrate 20 coupled to each other with a predetermined gap therebetween, and a liquid crystal layer 30 injected between the first substrate 10 and the second substrate 20. The first substrate 10 includes a TFT area having a TFT that performs a switching function, a pixel area (Pixel), and a storage CST.

The first substrate 10 includes a transparent glass substrate 11 and a plurality of gate lines 12 and a plurality of data lines 16 positioned on the transparent glass substrate 11. The plurality of gate lines 12 are arranged in one direction with a substantially constant distance therebetween. The plurality of data lines 16 are arranged with a substantially constant distance therebetween in a direction substantially perpendicular to the gate lines 12. The pixel area (Pixel) is defined by the gate lines 12 and the data lines 16.

A pixel electrode 18 is formed in each pixel area (Pixel), and a thin film transistor is formed at each crossing of the gate lines 12 and the data lines 16. The thin film transistor applies a data signal on the data line 16 to the pixel electrode 18 in response to a scan signal applied on the gate line 12.

The second substrate 20 includes a transparent glass substrate 21 and a black matrix layer 22. The black matrix layer 22 is formed on the transparent glass substrate 21 to block light transmitted outside the pixel area (Pixel) of the first substrate 10. Red (R), green (G) and blue (B) color filter layers 23 are formed to express color corresponding to each pixel area. A common electrode 24 is formed on each of the color filter layers 23.

A charge capacitor is formed over a portion of the gate line 12 and is connected in parallel to the pixel electrode 18. A first electrode of the charge capacitor uses a portion of the gate line 12, and a second electrode uses a metal pattern with an island shape made of the same material as a source electrode and a drain electrode.

The liquid crystal layer 30 of the liquid crystal display is aligned by an electric field between the pixel electrode 18 and the common electrode 24. The quantity of light transmitted through the liquid crystal layer 30 is controlled based upon an alignment direction of the liquid crystal layer 30, thereby displaying a desired image.

FIG. 3 schematically illustrates a configuration of a liquid crystal panel.

Referring to FIG. 3, the liquid crystal panel includes the first substrate 10, the second substrate 20, the liquid crystal layer 30, a first polarizing plate 50, a second polarizing plate 60, and a backlight unit 40. A first alignment layer 15 and a second alignment layer 25 are formed on the first substrate 10 and the second substrate 20, respectively, using a rubbing method.

The liquid crystal panel of FIG. 3 is a liquid crystal cell with anti-parallel alignment between the first and second polarizing plates. Examples of the anti-parallel alignment include an in-plane switching (IPS) mode liquid crystal cell and an electrically controllable birefringence (ECB) mode liquid crystal cell. The first polarizing plate 50 and the second polarizing plate 60 are set in a cross-Nicol configuration.

FIG. 3 shows the various elements of the liquid crystal cell spaced apart from one another. However, in fact, all the elements contact one another. Electrical and optical characteristics of the liquid crystal display are determined by alignment directions of the first and second alignment layers 15 and 25 and polarization directions of the first and second polarizing plates 50 and 60. In other words, because the electrical and optical characteristics of the liquid crystal display are determined by the combination of the alignment directions of the first and second alignment layers 15 and 25 and the polarization directions of the first and second polarizing plates 50 and 60, the alignment directions and the polarization directions (i.e., alignment axes and polarization axes) need to be accurately known.

Figure 4B:
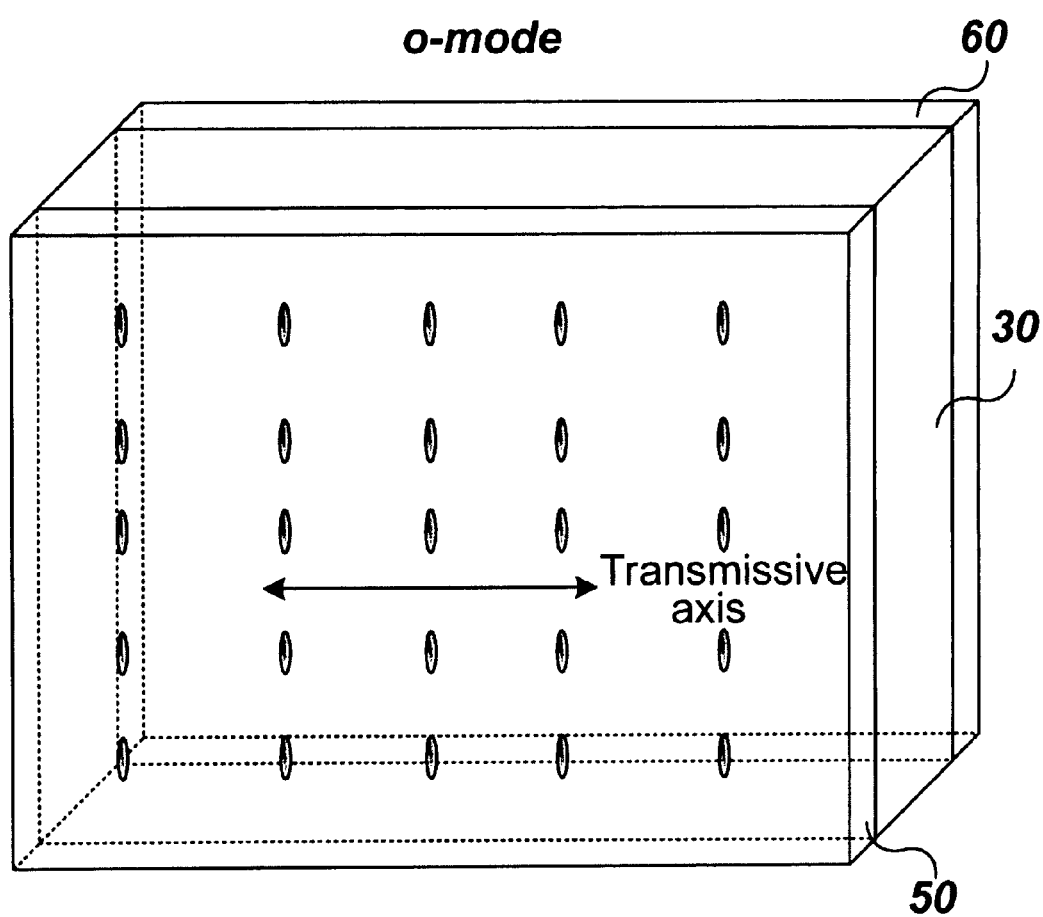

FIGS. 4A and 4B illustrate a polarization mode of a polarizing plate of a liquid crystal display according to an embodiment of the present invention.

Referring to FIGS. 4A and 4B, a polarizing plate may be classified as an extraordinary mode (e-mode) polarizing plate or an ordinary mode (o-mode) polarizing plate. The liquid crystal has both properties of the e-mode polarizing plate and properties of the o-mode polarizing plate.

In the e-mode, a transmissive axis of the first polarizing plate 50 and a long axis the liquid crystal are in an extraordinary state. In an o-mode, the transmissive axis of the first polarizing plate 50 and the long axis the liquid crystal are perpendicular to each other.

The first polarizing plate 50 is spaced apart from the second polarizing plate 60 with the liquid crystal layer 30 therebetween. The first polarizing plate 50 functions as a polarizer, and the second polarizing plate 60 functions as an analyzer.

FIG. 4a illustrates the e-mode in which the polarization direction of the polarizer 50 is horizontal to the plane and the polarization direction of the analyzer 60 is perpendicular to the plane.

FIG. 4b illustrates the o-mode in which the polarization direction of the polarizer 50 is perpendicular to the plane and the polarization direction of the analyzer 60 is horizontal to the plane.

The e-mode and the o-mode are polarization modes for absorbing light vibrating in a selected direction or transmitting only light vibrating in a selected direction.

Figure 5:
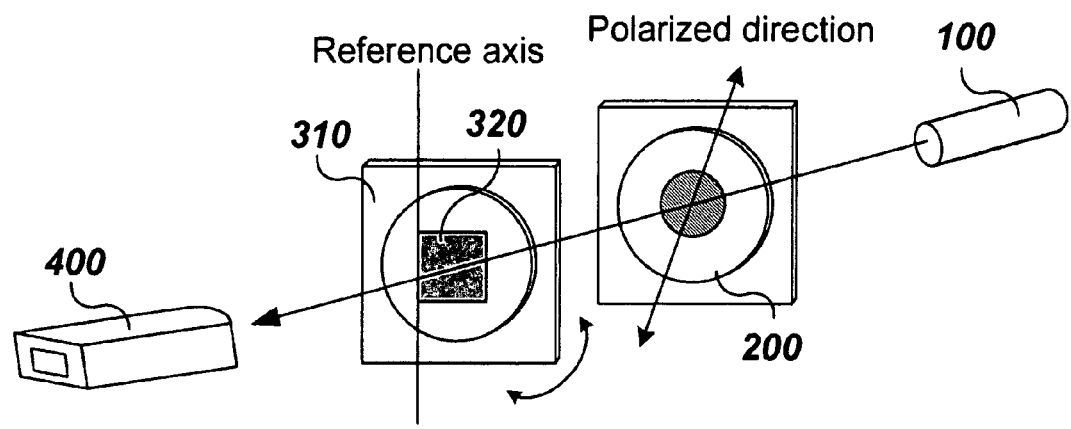
FIG. 5 illustrates a configuration of an apparatus for measuring a polarization direction of a polarizing plate of a liquid crystal display according to an embodiment of the present invention.

FIG. 5 illustrates a configuration of an apparatus for measuring a polarization direction of a polarizing plate of a liquid crystal display according to an embodiment of the present invention.

Referring to FIG. 5, the apparatus for measuring the polarization direction of the polarizing plate for the liquid crystal display includes a light source 100, a first polarizing plate 200, a sample holder 310, a sample 320, and a light detector 400 that are positioned in the order named.

The light source 100 provides light passing through the first polarizing plate 200 and the sample 320, and generally uses a laser light source.

The polarization direction of the first polarizing plate 200 is set relative to a reference axis of the sample holder 310.

The sample 320 is a polarizing plate to be measured, and it corresponds to the first polarizing plate 200. A polarization direction of the sample 320 is obtained by one half ((X2−1)/2) a difference (i.e., X2−X1) between a first angle X1, where the minimum quantity of light is detected when rotating the sample holder 310 when a first surface of the sample 320 faces the light source, i.e., a first direction, and a second angle X2, where the minimum quantity of light is detected when rotating the sample holder 310 when a second surface of the sample 320 faces the light source, i.e., a second direction. The sample 320 put into the sample holder 310 rotates along the reference axis in the azimuth direction.

The light detector 400 detects the light that is produced by the light source 100 and passes through the first polarizing plate 200 and the sample 320. The light detector 400 uses a photodetector or a luminance meter.

Accordingly, the reference axis is in a reference plane of the sample holder 310. Although the polarization direction of the first polarizing plate 200 is not accurately known, the polarization direction of the sample 320 is accurately measured using this simple method.

Figure 6:
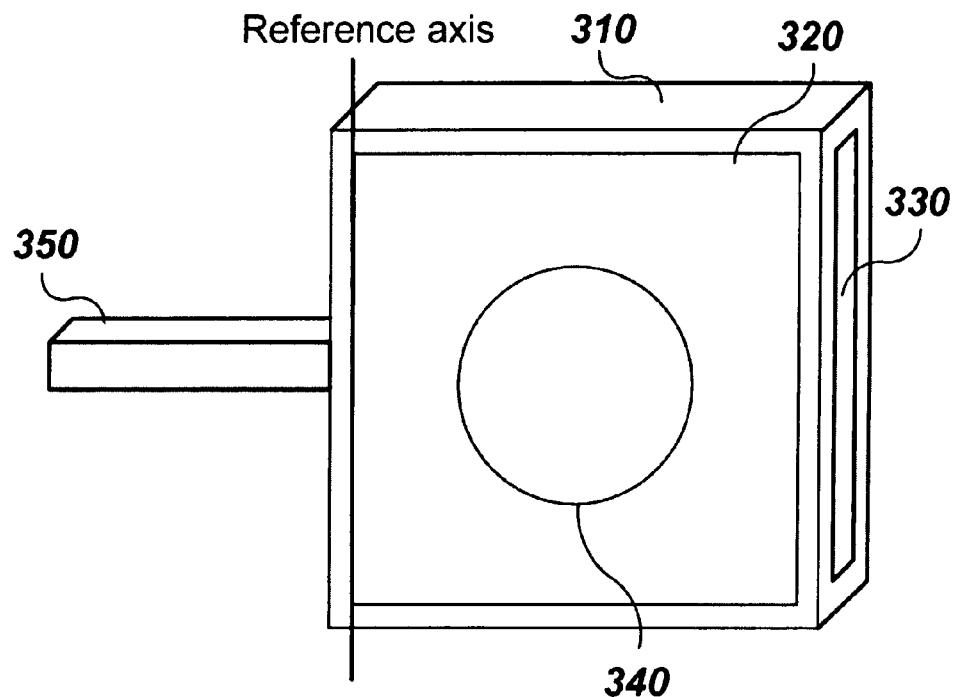
FIG. 6 illustrates an example of a sample holder of a polarization direction measuring apparatus according to an embodiment of the present invention.
Figure 7A:
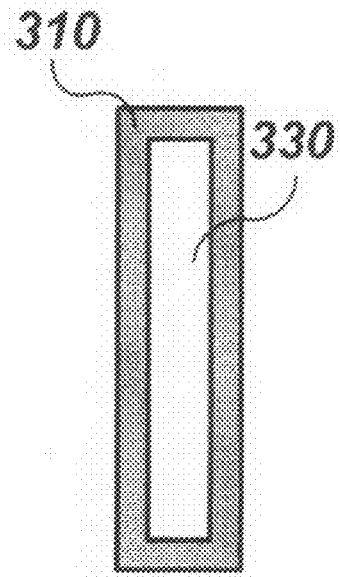
FIGS. 7A and 7B are cross-sectional views of the sample holder of FIG. 6.
Figure 7B:
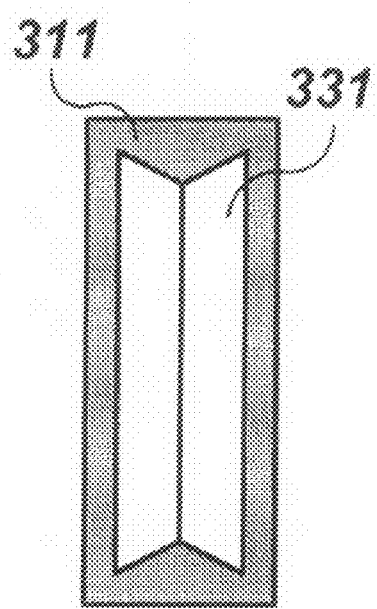

FIG. 6 illustrates an example of a sample holder of a polarization direction measuring apparatus according to an embodiment of the present invention. FIGS. 7A and 7B are cross-sectional views of the sample holder of FIG. 6.

Referring to FIG. 6, the sample holder 310 includes a housing into which the sample 320 is inserted, a first insertion opening 330, and a light transmission opening 340. The first insertion opening 330 is formed in one direction of the housing, and fastens the sample 320 inserted in the first direction. The light transmission opening 340 passes through the housing and transmits light passing through the first polarizing plate 200.

Referring to FIGS. 7A and 7B, the sample holder 310 may additionally include a second insertion opening 331. The shape of the second insertion opening 331 is symmetrical to the shape of the first insertion opening 330, and the second insertion opening 331 fastens the sample 320 inserted in the second direction.

In FIG. 7A, the sample holder 310 includes only the first insertion opening 330. In FIG. 7B, the sample holder 310 includes the first and second insertion opening 311 and 331 whose shapes are symmetrical to each other.

Further, the sample holder 310 may additionally include a grip 350 that is positioned at one side of the housing to rotate the housing.

The polarization direction measuring apparatus does not need to know the polarization direction of the first polarizing plate 200. Instead, the sample 320 may be inserted into the insertion opening of the sample holder 310 in a reverse direction. A method for measuring the polarization direction of the sample 320 is as follows.

First, after the sample 320 is put into the sample holder 310, the sample 320 is fastened in the insertion opening 330 along the reference axis.

Next, while the sample holder 310 rotates, the first angle X1 is measured at which the minimum quantity of light is detected using the light detector 400.

After the sample 320 is again put into the sample holder 310 in a second or reverse direction, the second angle X2 is measured at which the minimum quantity of light is detected using the light detector 400.

Then the polarization direction of the sample 320 to the reference axis is θ1, and θ1 is equal to (X2−X1)/2.

Figure 8A:
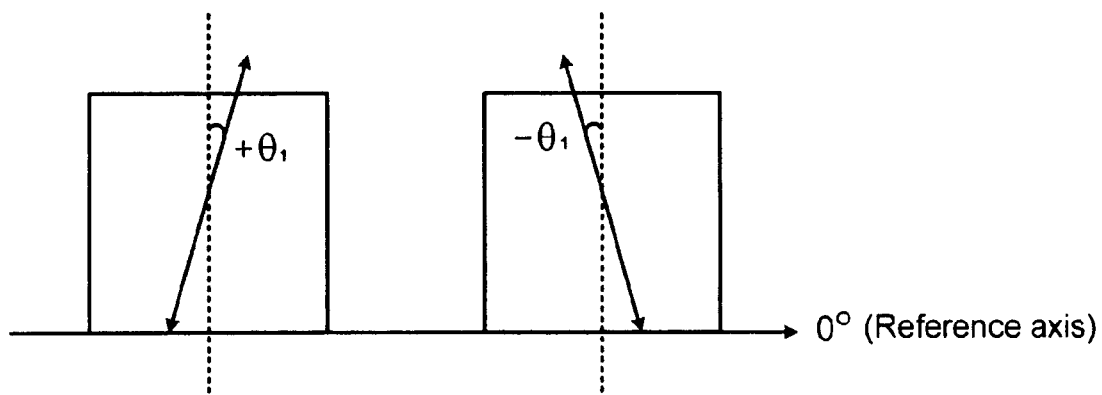
FIGS. 8A and 8B illustrate a process of measuring the polarization direction of a polarizing plate of a liquid crystal display according to an embodiment of the present invention.
Figure 8B:
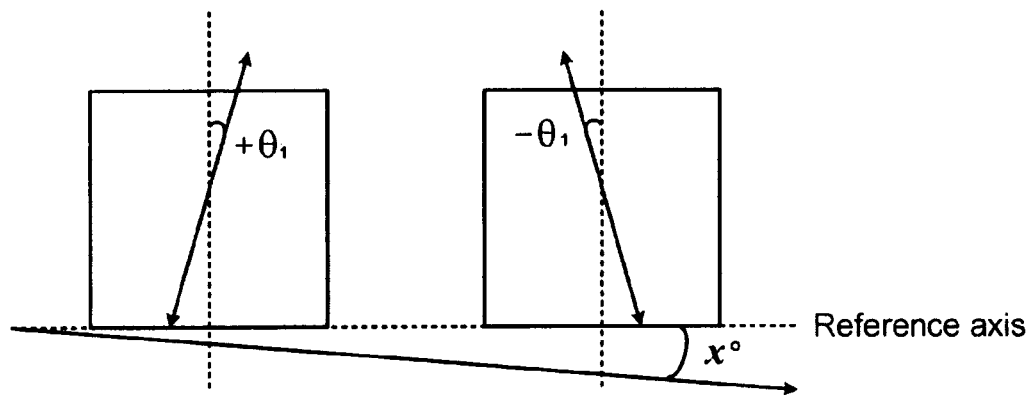

FIGS. 8A and 8B illustrate a process of measuring the polarization direction of a polarizing plate of a liquid crystal display according to an embodiment of the present invention.

FIG. 8A illustrates a case where the reference axis of the sample holder 310 is not inclined. FIG. 8B illustrates a case where the reference axis of the sample holder 310 is inclined at x°.

At the right of FIGS. 8A and 8B, the first angle X1 is measured when inserting the sample 320 into the sample holder 310 in the first direction, and the second angle X2 is measured when inserting the sample 320 into the sample holder 310 in the second direction.

When the polarization direction of the sample 320 is θ1, the following equations are satisfied: X1=−θ1+x, X2=+θ1+x, and X2−X1=2θ1. In other words, the polarization direction θ1 of the sample 320 is obtained irrespective of the inclination angle x° of the reference axis of the sample holder 310.

In other words, although the polarization direction of the first polarizing plate 200 is not known, the polarization direction of the sample 320 is obtained using the above-described measuring method by inserting the sample 320 into the sample holder 310 facing opposite directions.

Figure 9:
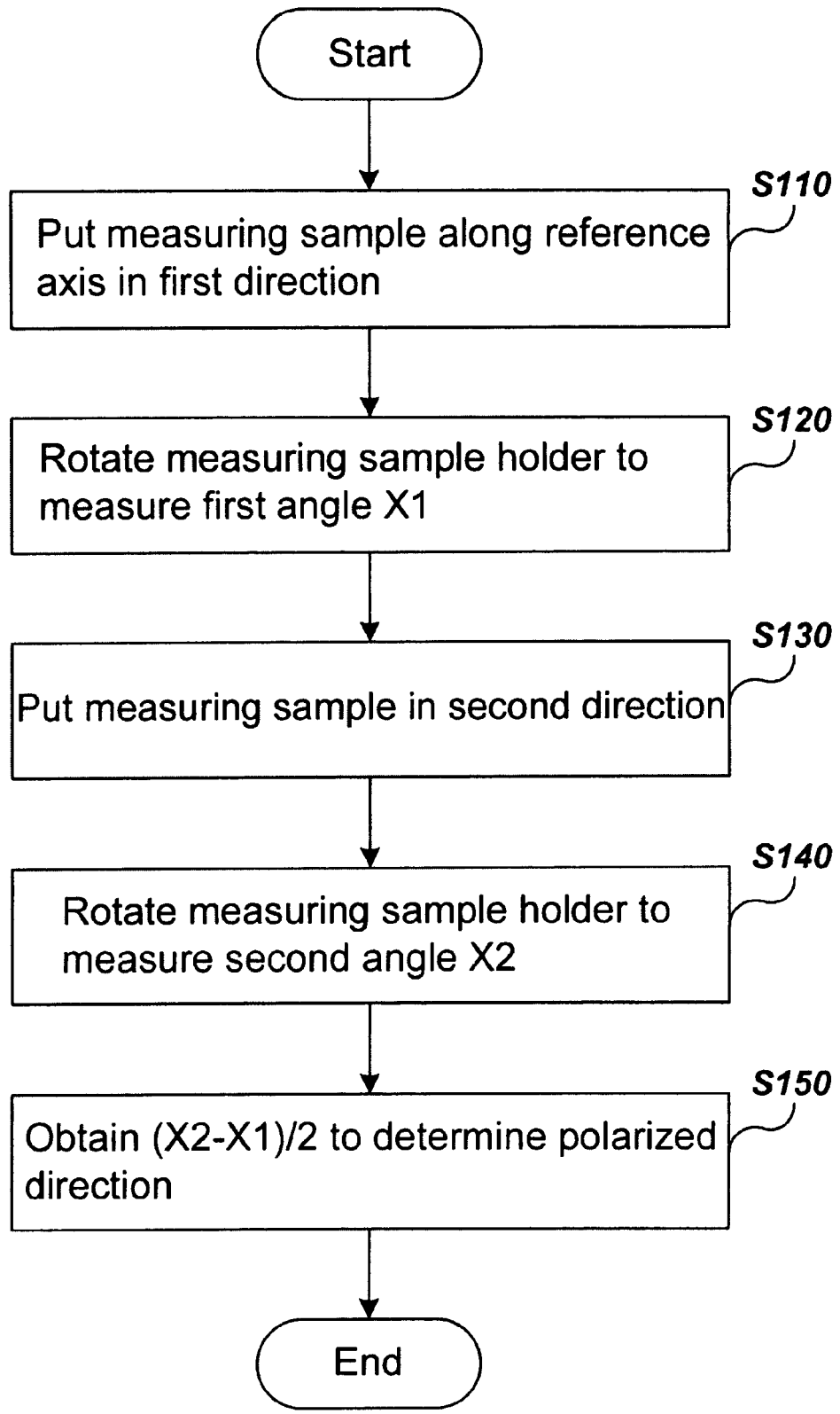
FIG. 9 is a flow chart of a method for measuring a polarization direction of a polarizing plate of a liquid crystal display according to an embodiment of the present invention.

FIG. 9 is a flow chart of a method for measuring a polarization direction of a polarizing plate of a liquid crystal display according to an embodiment of the present invention.

Referring to FIGS. 5 and 9, in the method for measuring the polarization direction of the polarizing plate of the liquid crystal display, the light source 100, the first polarizing plate 200 and the light detector 400 are aligned, and the sample 320 is then put into the sample holder 310 along the reference axis in the first direction in step S110.

The sample holder 310 is aligned between the first polarizing plate 200 and the light detector 400. The sample 320 is a second polarizing plate corresponding to the first polarizing plate 200 and is fastened in the sample holder 310 in each of the first direction and the second direction. The polarization direction of the first polarizing plate 200 is optionally set, and the reference axis of the sample holder 310 is in a reference plane of the sample holder 310.

While the sample holder 310 rotates in the azimuth direction, the first angle X1 at which the minimum quantity of light is detected is measured in step S120.

Next, the sample 320 is again put into the sample holder 310 in the second direction opposite to the first direction in step S130. The sample holder 310 is again aligned between the first polarizing plate 200 and the light detector 400.

While the sample holder 310 rotates in the azimuth direction, the second angle X2 at which the minimum quantity of light is detected is measured in step S140.

Finally, a relationship (X2−X1)/2 between the first angle X1 and the second angle X2 is calculated to obtain the polarization direction of the sample 320.

As described above, the method and the apparatus for measuring the polarization direction may obtain the polarization direction of the sample using only the reference axis of the sample holder without knowing the polarization direction of the reference polarizing plate. Accordingly, the polarization direction of the sample can be accurately measured using this simple method.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

What is claimed is:

1. A polarization direction measuring apparatus comprising:
    a first polarizing plate having an unknown polarization direction relative to a reference axis;
    a sample whose a polarization direction is to be measured;
    a rotatable sample holder on which the sample is mounted in a first direction and a second direction opposite to the first direction, wherein the sample holder rotates the sample along a reference axis in the azimuth direction;
    a light source that generates light passing though the first polarizing plate and the sample; and
    a light detector detecting light generated by the light source that passes though the first polarizing plate and the sample,
    wherein the polarization direction of the sample is obtained by one half a difference between a first angle, at which the minimum quantity of light is detected when rotating the sample put in the first direction, and a second angle, at which the minimum quantity of light is detected when rotating the sample put in the second direction.

2. The polarization direction measuring apparatus of claim 1, wherein the sample is a second polarizing plate corresponding to the first polarizing plate.

3. The polarization direction measuring apparatus of claim 1, wherein the reference axis is perpendicular to a reference plane of the sample holder.

4. The polarization direction measuring apparatus of claim 1, wherein the sample holder includes:
    a housing into which the sample is inserted;
    a first insertion opening that is positioned at one side of the housing and fastens the sample inserted in the first direction; and
    a light transmissive opening passing through the housing that transmits light passing through the first polarizing plate.

5. The polarization direction measuring apparatus of claim 4, wherein the sample holder further includes a second insertion opening with a shape that is symmetrical to the shape of the first insertion opening, the second insertion opening fastening the sample inserted in the second direction.

6. The polarization direction measuring apparatus of claim 4, wherein the sample holder further includes a grip positioned at a side of the housing that rotates the housing.

7. The polarization direction measuring apparatus of claim 1, wherein the light source is a laser light source.

8. The polarization direction measuring apparatus of claim 1, wherein the light detector includes one of a photodetector and a luminance meter.

9. A method of measuring a polarization direction comprising:
    aligning a light source, a first polarizing plate, and a light detector;
    inserting a sample into a sample holder in a first direction, wherein a reference axis of the sample holder aligns with the light source and the light detector;
    rotating the sample holder in an azimuth direction to measure a first angle at which a minimum quantity of light is detected;
    inserting the sample into the sample holder in a second direction opposite to the first direction;
    rotating the sample holder in the azimuth direction to measure a second angle at which a minimum quantity of light is detected; and
    obtaining a value corresponding to one half a difference between the first angle and the second angle to measure a polarization direction of the sample
    wherein putting the sample in the first direction includes fastening the sample into an insertion opening of the sample holder in the first direction and inserting the sample in the second direction and fastening the sample into the insertion opening of the sample holder in the second direction.

10. The method of claim 9, wherein the sample is a second polarizing plate corresponding to the first polarizing plate.

11. The method of claim 9, wherein when inserting the sample in the first direction and the second direction, the sample holder is aligned between the first polarizing plate and the light detector.

12. The method of claim 9, wherein in aligning the light source, the first polarizing plate, and the light detector, a polarization direction of the first polarizing plate is unknown.

13. The method of claim 9, wherein when putting the sample in the first direction, the reference axis is perpendicular to a reference plane of the sample holder.

14. The method of claim 9, wherein the light source is a laser light source.

15. The method of claim 9, wherein the minimum quantity of light in the first and second directions is detected using the light detector.

16. The method of claim 15, wherein the light detector includes one of a photodetector and a luminance meter.

* * * * *